United States Patent [19]

Schneider et al.

[11] Patent Number: 4,922,001

[45] Date of Patent: May 1, 1990

[54] CHIRAL SYNTHESIS UNITS FROM PROCHIRAL GLYCEROL

[75] Inventors: Manfred Schneider; Kurt Laumen; Detlef Breitgoff, all of Wuppertal; Dieter Wullbrandt, Hofheim am Taunus; Merten Schilingmann, Königstein/Taunus; Reinhold Keller, Bad Soden am Taunus, all of Fed. Rep. of Germany

[73] Assignee: Hoechst Aktiengesellschaft, Frankfurt am Main, Fed. Rep. of Germany

[21] Appl. No.: 75,761

[22] Filed: Jul. 20, 1987

[30] Foreign Application Priority Data

Jul. 22, 1986 [DE] Fed. Rep. of Germany ....... 3624703

[51] Int. Cl.$^5$ ............................................. C07C 69/76
[52] U.S. Cl. ................................. 560/112; 260/410.6; 560/187; 560/189; 560/61; 560/155; 560/173
[58] Field of Search ................. 560/112, 61, 155, 173, 560/187, 189; 260/410.6

[56] References Cited

PUBLICATIONS

Weber, A. et al., CA 102(17):146207u, 1985.
Baran, J., CA 87(5):39430m, 1977.
CA(102)(17):148998b, 1984.
Mueller, H., CA 106(17) 137922d.
Mueller et al., Tetrahedron, vol. 42, No. 5, 1986, pp. 1533–1538.
Baran et al., Journal of Organic Chemistry, vol. 42, No. 13, 1977, pp. 2260–2264.
Weber (Eur. J. Biochem., 146, 1985, pp. 323–329).

*Primary Examiner*—Paul J. Killos
*Attorney, Agent, or Firm*—Finnegan, Henderson, Farabow, Garrett and Dunner

[57] ABSTRACT

Differentiation of the two enantiotopic groups in prochiral glycerol derivatives gives chiral molecules directly, which in turn are easily converted either into the S-series or into the R-series by selective manipulation of the functional groups.

6 Claims, No Drawings

CHIRAL SYNTHESIS UNITS FROM PROCHIRAL GLYCEROL

DESCRIPTION

Chiral glycerol derivatives, for example (S)- and (R)-2,2-dimethyl-1,3-dioxolane-4-methanols 1 or the corresponding aldehydes (R) and (S) (2) have in the past been used intensively as units for the synthesis of enantiomerically pure naturally occurring substances and active compounds. Examples thereof are the preparation of phospholipids, PAF (platelet aggregation factor), β-blockers, (−)-γ-amino-β-hydroxybutyric acid (GABOB), prostaglandins, brefeldin A and many others.

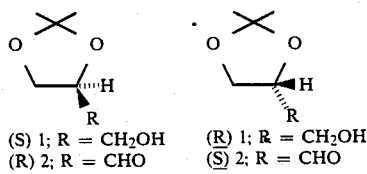

(S) 1; R = CH$_2$OH
(R) 2; R = CHO (R) 1; R = CH$_2$OH
(S) 2; R = CHO 1 and 2 can be converted into a large number of important intermediate products which can be used as starting materials for the preparation of lipids, carbohydrates, nucleotide analogs, naturally occurring substances and many other optically active molecules.

Enantiomerically pure chiral units with a basic glycerol structure have hitherto been obtained by synthesis from monosaccharides and amino acid, as can be seen from the following literature references: G. Wirk, W. Walter: Helv. Qim. Acta, 68, 1963 (1985); C. M. Lok et al.: Chem. Phys. Lipids 16, 115 (1976); and H. O. L. Fischer, E. Baer: J. Biol. Chem. 128, 463 (1939).

Glycerol has not so far been considered as an alternative source for such synthesis units. In view of the large amounts of lipids in fats and oils which are available from a regenerating biomass, a direct path from glycerol via a prochiral intermediate stage to chiral synthesis units is of considerable interest.

It has been found, surprisingly, that differentiation of the two enantiotopic groups in prochiral glycerol derivatives leads directly to chiral molecules, which in turn can easily be converted either into the S-series or into the R-series by selective manipulation of the functional groups.

The invention thus relates to:

1. The R- and S-enantiomers of the compound of the general formula I

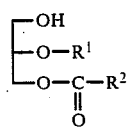

in which R$^1$ is an ether-forming protective group and R$^2$ represents a branched or, preferably, straight-chain alkyl group which has 1 to 18 carbon atoms and can optionally be substituted by halogen, hydroxyl, alkoxy with 1 to 3 carbon atoms, phenyl, phenoxy and/or thienyl, it being possible for a phenyl or phenoxy group to be substituted by alkyl, amine, hydroxyl, halogen and alkoxy.

2. A process for the preparation of the R- or S-enantiomers of the compound of the abovementioned general formula I, which comprises selectively esterifying a hydroxyl group from the compound of the general formula II

in which R$^1$ has the abovementioned meaning and R$^3$ is hydrogen or

in which R$^2$ likewise has the abovementioned meaning,
by incubation with hydrolases,
if R$^3$ is hydrogen, with the compound of the general formula

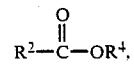

in which R$^2$ has the abovementioned meaning and R$^4$ denotes C$_1$ to C$_6$ alkyl or alkenyl which is straight-chain or branched and can be substituted by halogen, hydroxyl, alkoxy or nitro, or
if R$^3$ denotes the group

selectively splitting off an ester group.

The invention is illustrated in more detail below and defined in the claims.

The compound of the general formula II is an intermediate in the preparation of the compound of the general formula I. The starting compound of the general formula II for the preparation of the compound I can easily be prepared by processes which are known per se: N. Bagett et al., Chem. Soc. 2574 (1960). The compound of the general formula I is obtained from the compound of the general formula II by selective enzymatic hydrolysis with the aid of hydrolases. Only one of the two acyl groups is to be split off here, so that no undesirable by-products are formed. R$^1$ both in the compound of the general formula I and in the compound of the general formula II denotes an ether-forming protective group. Suitable examples are methyl ethers, which can optionally be substituted, such as, for example, methoxymethyl, 2-methoxyethoxymethyl and tetrahydropyranyl, or substituted ethyl ethers, such as, for example, benzyl, p-methoxybenzyl, o-nitrobenzyl, p-nitrobenzyl, p-halobenzyl, p-cyanobenzyl and triphenylmethyl, or silyl ethers, such as, for example, trimethylsilyl and t-butyldiphenylsilyl.

Benzyl or substituted benzyl is preferably used as the protective group for R$^1$.

The protective group R$^2$ represents a branched or, preferably, straight-chain alkyl group which has 1 to 18 carbon atoms, preferably 1 to 5 carbon atoms, and can optionally be substituted by halogen, hydroxyl, alkoxy with 1 to 3 carbon atoms, phenyl, phenoxy and/or thienyl, it being possible for a phenyl or phenoxy group to be substituted by alkyl, amine, hydroxyl, halogen and alkoxy.

The R- or S-configuration of the compound of the general formula I can be formed, depending on the selectivity of the enzyme. Suitable enzymes are, inter alia, esterases and lipases from various microorganisms, for example from *Candida cylindracea,* Mucor sp. or *Chromobacterium viscosum,* or also from the pig liver or pig pancreas. Lipases from the pig pancreas (E.C. 3.1.1.3) or from Pseudomonas spec., such as, for example, lipoproteinlipase (E.C. 3.1.1.34) are particularly preferred. The enzymes can be used both in soluble form and in the form fixed to a carrier, in accordance with the prior art [European Patent 220,593; Laumen et al., Tetrahedron Letters 26, 407 (1985)].

The lipoproteinlipase essentially splits off only one acyl group enantioselectively. A product of high enantiomer purity is obtained. If lipase from the pig pancreas is used for the hydrolysis of the compound of the general formula II in which $R^3$ denotes the group

the selectivity and the formation of the by-product in which both ester groups are split off depend on the substrate concentration and the ratio of substrate to enzyme. If higher enzyme and substrate concentrations are used, a high conversion into the product I of high enantiomer purity is achieved in a few hours. By increasing the solubility of the compound of the general formula II in the aqueous reaction medium by adding solvents which are water-miscible to a certain degree or entirely but do not substantially reduce the enzyme activity or change its specificity, the rate of reaction can be increased. Suitable solvents are cyclic ethers, such as tetrahydrofuran and dioxane, ($C_1$-$C_3$)-alkanols, acetone or dimethylsulfoxide, or dimethylformamide.

The reaction proceeds at 10° to 50° C., preferably 20° to 35° C. At higher temperatures, the enzymes are increasingly deactivated, unless the proteins are thermophilic. At lower temperatures, the reaction proceeds too slowly. The pH is between 5 and 8, preferably between 6.5 and 7.5. The enzyme concentration can vary within wide limits, especially since, as mentioned above, it can be chosen according to the substrate concentration. An enzyme concentration of 500 to 20,000 U/mMol of substrate, preferably 600 to 8,000 U/mMol of substrate, is advantageously chosen at a substrate concentration of 0.05 to 2.5 mol/l, preferably 0.2 to 1.5 mol/l. The lipoprotein lipase can be used in smaller amounts, for example 10 to 2,000 U/mMol of substrate. One unit (U) of enzyme activity designates the amount which hydrolytically splits off 1.0 microequivalent of fatty acid from a triglyceride per minute at pH 7.0 and at a temperature of 37° C. The optimum reaction conditions of course depend on what enzyme is used. However, they can easily be determined by the expert.

As mentioned, not only can the hydrolysis be carried out with the aid of the process according to the invention, but at very low water concentrations of about 0.1 to 5% of $H_2O$, preferably 0.25-1.5%, based on the weight of the reaction batch, alcoholysis of the compound of the general formula II in which $R^3$ denotes hydrogen can also be carried out. The reaction conditions for the alcoholysis are otherwise identical to those of the hydrolysis. Since the same enantiotopic group is recognized by the enzyme both during hydrolysis and during alcoholysis, if prochiral substrates are used the opposite absolute configurations in each case result, as is shown, for example, in the following diagram.

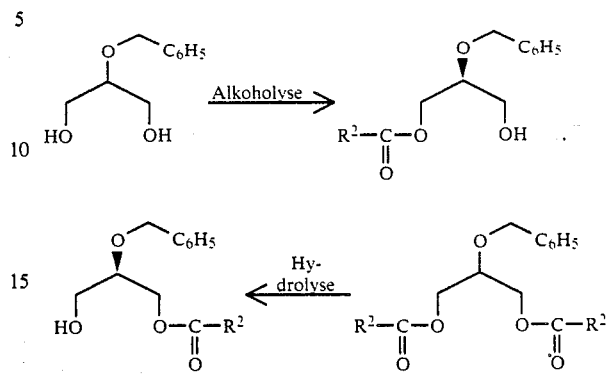

The compound of the general formula II is the intermediate and therefore the key substance for the preparation of other compounds en route to pharmaceutically active substances as mentioned above, for example. These are obtained by reaction of the compound I with reagents which are suitable as a protective group for the hydroxyl group and which can be split off again. Preferred protective groups give dihydropyran, trityl halide, toluenesulfonic acid halide, trisubstituted silyl halide, methoxymethyl halide or 2-methoxyethoxymethyl halide. The reaction conditions under which protective groups are introduced and can be split off again are to be found in the appropriate literature, for example: Protective Groups in Organic Synthesis T. W. Greene (Wiley Intersciences, 1981) or J. F. W. McOmie (Plenum Press, London, 1973).

Subsequent splitting off of the $R^2CO-$ group gives the corresponding compounds with a free hydroxyl group, which are in turn the starting substance for the abovementioned pharmaceutical compounds.

The reaction conditions under which the $R^2CO-$ group can be split off are known from the literatue. The reaction is carried out, for example in a weakly basic medium with an alcohol as the solvent ($K_2CO_3$/methanol, $NH_3$/methanol, NaOH/pyridine or ethanol) or in the acid range (HCL/acetone).

Synthesis units of both enantiomeric series can be prepared by the selective manipulations described above for the intermediate I, depending on the configuration thereof. For example, if the R-enantiomer of the compound I is used as the starting substance, the R- or S-enantiomer of the resulting compounds are obtained, depending on what protective group is introduced. If the $R^2CO-$ groups are then split off, the S-enantiomer of the resulting hydroxyl compound is obtained in all cases. This S-hydroxyl compound can in turn be reacted with reagents which give corresponding protective groups, whereupon, after aplitting off the original protective groups, the R-hydroxyl compounds are obtained. The equation on page 18 is intended to illustrate this state of affairs by way of example.

The great synthetic benefit of the compound II is illustrated by its ease of conversion into the R- or S-series. A large number of useful chiral glycerol derivatives of both enantiomeric series can be prepared with the aid of these intermediates. With simple glycerol as the starting material, an alternative chemoenzymatic route to such synthesis units has been opened up for the first time. In view of the large amounts of lipids, in particular fats and oils, from a regenerating biomass, this fundamental work opens up an economic access to important units in the synthesis of natural substances and active compounds.

The invention is illustrated in detail in the following examples. Unless indicated otherwise, percentage data relate to the weight.

EXAMPLES

Enzymatic hydrolysis of 2-0-benzylglycerol 1,3-diacetate 1. 50 mMol (13.3 g) of 2-0-benzylglycerol 1,3-diacetate are suspended in 100 ml of 0.1M phosphate buffer (pH 7, 20° C.) and 200 mg of lipase from the pig pancreas (PPL, EC 3.1.1.3) are added. The pH is kept constant at pH 7 by continuous addition of 1N NaOH from an autoburette. The hydrolysis is interrupted after a consumption of 50 ml of 1N NaOH (about 4 hours) and the reaction mixture is extracted continuously with 150 ml of ether (about 12 hours). The organic phase is dried over $MgSO_4$, the solvent is stripped off and the residue is chromatographed on silica gel 60 (70–230 mesh, diethyl ether/hexane 1:2).

|  |  | Rf |
|---|---|---|
| Fraction 1: | 2-0-benzylglycerol 1,3-diacetate | 0.7 |
| Fraction 2: | R-1-hydroxy-2-0-benzylglycerol 3-acetate | 0.4 |
| Fraction 3: | 2-0-benzylglycerol |  |

Yield of R-1-hydroxy-2-0-benzylglycerol 3-acetate: 5.3 g (47%).

Optical rotation: $[\alpha]D^{20}=8.98°$ (c 2.78 ethanol); $[\alpha]D^{20}+12.75°$; $[\alpha]_{365}20+40.5°$ (c 1.796 chloroform + 1% of ethanol).

Optical purity: 60% e.e.

2. 100 mMol (26.6 g) of 2-0-benzylglycerol 1,3-diacetate are suspended in 200 ml of a mixture of 175 ml of 0.1M phosphate buffer (pH 7, T=20° C.) and 25 ml of tetrahydrofuran, and 250 mg of lipase from the pig pancreas (PPL, E.C. 3.1.1.3) are added. The pH is kept constant at pH 7 by continuous addition of 1N NaOH from an autoburette. The hydrolysis is interrupted after a consumption of 96 ml of 1N NaOH (4 hours) and the reaction mixture is extracted continuously with 150 ml of diethyl ether. The organic phase is dried over $MgSO_4$, the solvent is stripped off and the residue is chromatographed over silica gel 60 (70–230 mesh, diethyl ether/hexane 1:2).

Yield of R-1-hydroxy-2-0-benzylglycerol 3-acetate: 8.7 g (40%).

Optical rotation: $[\alpha]_D20-12°$, $[\alpha]_{365}20-40.3°$ (c 2.99 in ethanol); $[\alpha]_D20+16.75°$, $[\alpha]_{365}20+52.6°$ (c 1.74 chloroform + 1% ethanol).

Optical purity: 84% e.e.

3. 150 mMol (40 g) of 2-0-benzylglycerol 1,3-diacetate are suspended in 150 ml of 0.1M phosphate buffer (pH 7, T=20° C.), and 5 g of lipase from the pig pancreas (PPL, E.C. 3.1.1.3) are added. The pH is kept constant at pH 7 by continuous addition of 1N NaOH from an autoburette. The hydrolysis is interrupted after a consumption of 155 ml of 1N NaOH (about 1 hour) and the mixture is extracted continuously with diethyl ether. The organic phase is dried over $MgSO_4$, the solvent is stripped off and the residue is chromatographed over silica gel 60 (70–230 mesh, diethyl ether/hexane 1:2).

Yield of R-1-hydroxy-2-0-benzylglycerol 3-acetate: 22 g (75%)

Optical rotation: $[\alpha]_D20=13.10°$ (c 2.85 in ethanol); $[\alpha]_D20+17.4°$, $[\alpha]_{365}20+54.9°$ (c 1.85 chloroform + 1% ethanol).

Optical purity: 90% e.e.

4. 50 mMol (13.3 g) of 2-0-benzylglycerol 1,3-diacetate are suspended in 100 ml of 0.1M phosphate buffer (pH 7, T=20° C.), and 50 mg of lipoprotein lipase (LPL, EC 3.1.1.34) are added. The pH is kept constant at pH 7 by continuous addition of 1N NaOH from an autoburette. The hydrolysis is interrupted after a consumption of 53 ml of 1N NaOH (6 hours) and the reaction mixture is extracted continuously with diethyl ether. The organic phase is dried over $MgSO_4$, the solvent is stripped off and the residue is chromatographed over silica gel 60 (70–230 mesh; diethyl ether/hexane 1:2).

Yield of R-1-hydroxy-2-0-benzylglycerol 3-acetate: 8.4 g (75%).

Optical rotation: $[\alpha]_D20-13.2°$ (c 2.95 in ethanol); $[\alpha]_D20+17.6°$, $[\alpha]_{365}20+55.2°$ (c 1.7 chloroform + 1% ethanol).

Optical purity: 91% e.e.

5. 100 mMol (26.6 g) of 2-0-benzylglycerol 1,3-diacetate are suspended in 1,500 ml of 0.1M phosphate buffer (pH 7, T=20° C.), and 50 mg of lipoprotein lipase (LPL, EC 3.1.1.134) are added. The pH value is kept constant at pH 7 by continuous addition of 1N NaOH from an autoburette. The hydrolysis is interrupted after a consumption of 110.7 ml of 1N NaOH (8 hours) and the reaction mixture is extracted continuously with diethyl ether. The organic phase is dried over $MgSO_4$, the solvent is stripped off and the residue is chromatographed over silica gel 60 (70–230 mesh, diethyl ether/petroleum ether 5:1). In contrast to Example 4, 2-0-benzylglycerol 1,3-diacetate was no longer to be detected.

Yield of R-1-hydroxy-2-0-benzylglycerol 3-acetate: 17 g (77%).

Optical rotation: $[\alpha]_D20+16.8°$, $[\alpha]_{365}20+52.2°$ (c 1.93 chloroform + 1% ethanol).

Optical purity: 85% e.e.

6. Preparation of (R)-1-0-acetyl-2-0-benzylglycerol 3-0-(2-tetrahydropyranyl) ether and (S)-2-0-benzylglycerol 3-0-(2-tetrahydropyranyl) ether (mixture of the diastereomers)

5.2 g (23.2 mMol) of R-1-hydroxy-2-0-benzylglycerol 3-acetate are dissolved in 30 ml of $CH_2Cl_2$ and the solution is stirred overnight with 5 ml of dihydropyran and 100 mg of p-toluenesulfonic acid. The reaction mixture is washed with saturated $NaHCO_3$ solution and the organic phase is dried with $MgSO_4$ and concentrated on a rotary evaporator. Chromatography of the residue on silica gel (diethyl ether/petroleum ether 1:2) gives 6.72 g (94%) of a product, $[\alpha]_D20-0.57°$; $[\alpha]_{365}20-2°$ (c 1.4 chloroform + 1% of ethanol). The material thus obtained was dissolved in 50 ml of methanol and the solution was stirred with 2 g of $K_2CO_3$ for 5 hours. After concentration of the solution on a rotary evaporator, the residue is taken up in 100 ml of diethyl ether, the mixture is filtered over silica gel and the filtrate is concentrated on a rotary evaporator. 5.5 g (95%) of 2-0-benzylglycerol-3-0-(2-tetrahydropyranyl) ether are obtained.

Optical rotation: $[\alpha]_D 20 -1°$, $[\alpha]_{365} 20 -3.2°$ (c 2.05 chloroform + 1% of ethanol).

7. Preparation of (S)-1-acetoxy-2-0-benzylglycerol 3-0-tosylate 8 g (35.7 mMol) of R-1-hydroxy-2-0-benzylglycerol 3-acetate are dissolved in 60 ml of absolute carbon tetrachloride, and 20 ml of absolute pyridine and 6.9 g of toluenesulfonyl chloride are added. The mixture is stirred at room temperature for 24 hours. 200 ml of $H_2O$ are then added. The organic phase is separated off and the aqueous phase is extracted with $2 \times 100$ ml of diethyl ether. The combined organic phases are washed with $2 \times 50$ ml of 2N HCl and $2 \times 50$ ml of $NaHCO_3$ solution. They are dried over $MgSO_4$ and the solvent is stripped off (crude yield 12.3 g). Column chromatography (diethyl ether/hexane 1:1) gives 10.65 g (78%) of (S)-1-acetoxy-2-0-benzylglycerol 3-0-tosylate:

Optical rotation: $[\alpha]_D 20 -16.7°$, $[\alpha]_{365} 20 -52°$ (c 1.14 chloroform + 1% of ethanol).

Optical purity: 91% e.e.

Preparation of (S)-2-0-benzylglycerol 1-0-tosylate 10.65 g (28 mMol) of 1-acetoxy-2-0-benzylglycerol 3-0-tosylate are stirred in a mixture of 100 ml of 1N HCl and 100 ml of acetone at room temperature for 24 hours (thin layer chromatography control). Solid $NaHCO_3$ is then added until the mixture is neturalized. After the undissolved $NaHCO_3$ has been filtered off, the filtrate is extracted with $3 \times 300$ ml of diethyl ether and the combined organic phase is dried over $MgSO_4$. After the solvent has been stripped off, 10.75 g of crude product remain, chromatography of which on silica gel (diethyl ether/hexane 3:1) gives 8.65 g (90%) of (S)-2-0-benzylglycerol 1-0-tosylate:

Optical rotation: $[\alpha]_D 20 -33°$, $[\alpha]_{365} 20 -116°$ (c 1.78, chloroform + 1% of ethanol).

Preparation of (S)-glycerol 1-0-tosylate 6 g (24.4 mMol) of (S)-2-0-benzylglycerol 1-0-tosylate are dissolved in 150 ml of distilled tetrahydrofuran and hydrogenated with the addition of 300 mg of palladium-on-charcoal (10%) at room temperature under normal pressure for 24 hours, with stirring. The catalyst is filtered off and washed with tetrahydrofuran. The solvent is removed in vacuo, the residue is taken up in 100 ml of diethyl ether and the mixture is filtered over a short silica gel column.

Removal of the solvent gives 4 g (91%) of (S)-glycerol 1-0-tosylate:

Optical rotation: $[\alpha]_D 25 -8.41°$, $[\alpha]_{365} 25 +26.1°$ (c=1.028 in methanol).

Recrystallization from diethyl ether/n-hexane (1:2) gives 3.2 g (73%) of (S)-glycerol 1-0-tosylate as colorless needles:

Melting point 61.5°–62° C.

Optical rotation: $[\alpha]_D 25 +9.45°$, $[\alpha]_D 25 +29°$ (c=0.75 in methanol).

8. Preparation of (S)-1-acetoxy-2-0-benzylglycerol 3-0-(diphenyl-t-butyl-silyl) ether 3.0 g (13.4 mMol) of R-1-hydroxy-2-0-benzylglycerol 3-acetate are dissolved in 50 ml of absolute carbon tetrachloride, 10 ml of absolute pyridine, 0.5 g of dimethylaminopyridine and 3.7 g of diphenyl-tert.-butylsilyl chloride are added and the mixture is stirred at room temperature for 26 hours. 200 ml of $H_2O$ are then added, the organic phase is separated off and the aqueous phase is extracted with $2 \times 100$ ml of diethyl ether. The combined organic phases are washed with $2 \times 50$ ml of 2N HCl and then $2 \times 50$ ml of $NaHCO_3$ solution. They are dried over $MgSO_4$ and the solvent is stripped off (crude yield 5.6 g). Chromatography on silica gel (diethyl ether/hexane 5:2) gives 4.5 g of (S)-1-acetoxy-2-0-benzylglycerol 3-0-(diphenyl-t-butyl-silyl) ether (75%):

Optical rotation: $[\alpha]_D 20 -6.3°$, $[\alpha]_{365} 20 -20°$ (c 2.29 chloroform + 1% of ethanol).

Preparation of (S)-2-0-benzyl 1-0-(diphenyl-t-butyl-silyl) ether 4.5 g (9.7 mMol) of (S)-1-acetoxy-2-0-benzylglycerol 3-0-(diphenyl-t-butyl-silyl) ether are dissolved in 60 ml of methanol, and 200 mg of $K_2CO_3$ are added. The mixture is stirred at room temperature for 18 hours, the methanol is stripped off and the residue is taken up in diethyl ether. The organic phase is filtered over a little silica gel. After the diethyl ether has been distilled off, the residue is chromatographed over silica gel (mobile phase diethyl ether/hexane 2:1). 1.73 g (42%) of (S)-2-0-benzyl 1-0-(diphenyl-5-butylsilyl) ether are obtained:

Optical rotation: $[\alpha]_D 20 -12.6°$, $[\alpha]_{365} 20 -40.5°$ (c 1.02 chloroform + 1% of ethanol).

2.17 g (48%) of (S)-1-acetoxy-2-0-benzylglycerol 3-0-(diphenyl-butyl-silyl) ether are not reacted.

9. Preparation of (R)-1-acetoxy-2-0-benzyl 3-0-tritylglycerol 5 g (22.3 mMol) of R-1-hydroxy-2-0-benzylglycerol 3-acetate are dissolved in 60 ml of absolute carbon tetrachloride, and 10 ml of absolute pyridine and 500 mg of dimethylaminopyridine are added. 6.2 g of trityl chloride are added and the mixture is stirred at room temperature for 48 hours. 200 ml of $H_2O$ are then added, the organic phase is separated off and the aqueous phase is extracted with $2 \times 250$ ml of diethyl ether. The combined organic phases are dried over $MgSO_4$ and the solvent is stripped off (crude yield 9.23 g).

Column chromatography (diethyl ether/hexane 1:2) gave 6.43 g (62%) of (R)-1-acetoxy-2-0-benzyl 3-0-tritylglycerol:

Optical rotation: $[\alpha]_D 20 -12.6°$, $[\alpha]_{365} 20 -42.5°$ (c 1.29 chloroform + 1% of ethanol).

Preparation of (S)-2-0-benzyl-1-0-tritylglycerol 6.43 g (12.8 mMol) of (R)-1-acetoxy-2-0-benzyl 3-0-tritylglycerol are reacted with $K_2CO_3/MeOH$ in accordance with Example 7. Crude yield 4.2 g.

Column chromatography on silica gel (diethyl ether/hexane 5:2) gives 3.64 g (62%) of (S)-2-0-benzyl-1-0-tritylglycerol:

Optical rotation: $[\alpha]_D 20 -20.3°$, $[\alpha]_{365} 20 -65°$ (c 1.46 chloroform + 1% of ethanol).

The product thus obtained is dissolved in boiling hexane and crystallized out at 4° C.:

Melting point 77°–79° C.;

Optical rotation: $[\alpha]_D 20 -23.6°$, $[\alpha]_{365} 20 -76°$ (c 1.49 chloroform + 1% of ethanol).

10. Preparation of (S)-1-0-acetyl-2-0-benzylglycerol 1.82 g of 2-0-benzylglycerol are dissolved in 18 g of absolute ethyl acetate and, after addition of small amounts of water (0.25–1.5% (Table 1)), 250 mg of lipase from Pseudomonas sp. are added and the mixture is stirred at room temperature. The reaction is monitored by gas chromatography. The reaction mixture is filtered and the lipase is used again. The filtrate is freed from the solvent and the residue is separated by chromatography on silica gel (mobile phase: diethyl ether/petroleum ether 1:2)

(S)-1-0-acetyl-2-0-benzylglycerol (Rf 0.3) 1.92 g (86%).

Optical rotation: $[\alpha]_D 20 -16.2°$; $[\alpha]_{365} 20 -51.4°$ c 1.76 chloroform + 1% of ethanol.

TABLE 1

Alcoholysis of ethyl acetate in the presence of 2-0-benzylglycerol and the lipase from Pseudomonas sp.

| Time (h) | Addition of water | | | | | | | |
|---|---|---|---|---|---|---|---|---|
| | 0.25% | | 0.5% | | 1.0% | | 1.5% | |
| | % 2⁺ | % 3* | % 2 | % 3 | % 2 | % 3 | % 2 | % 3 |
| 17.0 | 17.4 | — | 21.1 | — | 29.8 | <0.5 | 42.7 | 1.1 |
| 41.0 | 35.7 | <0.5 | 36.9 | <0.5 | 52.7 | 1.5 | 67.5 | 3.9 |
| 60.0 | 46.2 | 0.6 | 52.5 | 0.9 | 73.5 | 2.2 | 82.7 | 6.4 |
| 87.0 | 51.3 | 1.0 | 60.1 | 1.2 | 80.4 | 3.2 | 84.9 | 7.3 |
| 108.0 | 55.9 | 1.0 | 67.9 | 1.1 | 85.8 | 3.6 | 87.5 | 10.4 |
| 133.0 | 63.5 | 1.1 | 66.9 | 1.5 | 83.7 | 4.3 | 84.3 | 12.1 |

⁺(S)-1-0-acetyl-2-0-benzylglycerol = 2
*1,3-0-diacetyl-2-0-benzylglycerol = 3

EXAMPLE 11

10 mmol of 2-0-benzylglycerol were reacted in accordance with Example 10, using other lipases and with addition of cosolvents and various acetates.

The results are listed in Table 2:

TABLE 2

| Enzyme | [mg] | Ethyl acetate | [ml] | Cosolvent | (S)-2 [%] | Optical purity [% ee] |
|---|---|---|---|---|---|---|
| Lipase Pseudomonas sp. | 250 | ethyl | 18 | — | 86 | 84 |
| Lipase from pig pancreas | 500 | ethyl | 18 | — | 59 | 62 |
| Lipase from Chromobacterium vis. | 250 | ethyl | 18 | — | 84 | 55 |
| Lipoprotein Lipase | 30 | ethyl | 18 | — | 63 | 40 |
| *Lipase Pseudomonas sp. | 200 | trichloroethyl | 20 | — | 37 | 85 |
| **Lipase Pseudomonas sp. | 200 | isopropenyl | 20 | — | 5 | — |
| **Lipase Pseudomonas sp. | 200 | " | 1 | THF (20 ml) | 12 | — |
| Lipase Pseudomonas sp. | 200 | vinyl | 1 | THF (20 ml) | 80 | 85 |
| ***Lipase Pseudomonas sp. | 200 | vinyl | 20 | — | 45 | 96 |

THF = tetrahydrofuran
*no addition of water
**conversion to (S)-2 after 50 and 90 hours (S)-2: S-1-O-acetyl-2-O-benzylglycerol
***formation of 50% of 1,3-O-diacetyl-2-O-benzylglycerol
ee enantiomer excess

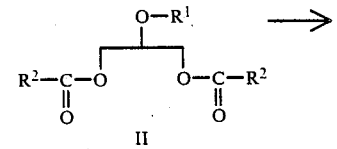

II

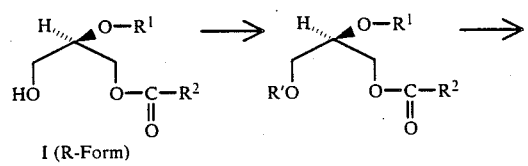

I (R-Form)

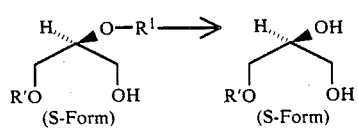

(S-Form)      (S-Form)

-continued

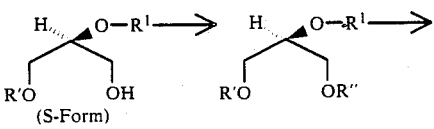

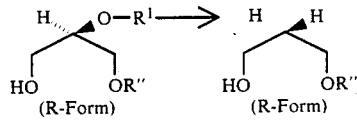

(R-Form)      (R-Form)

*R— or S-form, depending on the substituent
R' and R": protective groups

We claim:

1. A process for the preparation of an R- or S-enantiomer of a compound of the formula I

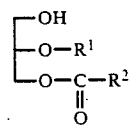

in which $R^1$ is an ether-forming protective group and $R^2$ represents a branched or, preferbly, straight-chain alkyl group which has 1 to 18 carbon atoms and can optionally be substituted by halogen, hydroxyl, alkoxy with 1 to 3 carbon atoms, phenyl, phenoxy, and/or thienyl, it being possible for a phenyl or phenoxy group to be substituted by alkyl, amine, hydroxyl, halogen or alkoxy, which comprises selectively esterifying a hydroxyl group from the compound of the formula II

in which $R^1$ has the above-mentioned meaning and $R^3$ is hydrogen or

in which $R^2$ likewise has the above-mentioned meaning, by incubation with a hydrolase, if $R^3$ is hydrogen, with the compound of the formula

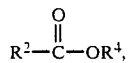

in which $R^2$ has the above-mentioned meaning and $R^4$ denotes $C_1$ to $C_6$ alkyl or alkenyl which is straight-chain or branched and can be substituted by halogen, hydroxyl, alkoxy or nitro, or which comprises selectively splitting off an ester group by incubation with a hydrolase if $R^3$ denotes the group

in which $R^2$ has the above meaning.

2. The process as claimed in claim 1, wherein a benzyl group or a substituted benzyl group is used for $R^1$.

3. The process as claimed in claim 1, wherein an esterase or lipase is used as the hydrolase.

4. The process as claimed in claim 3, wherein lipase from the pig pancreas (E.C. 3.1.1.3) or lipoprotein lipase (E.C. 3.1.1.34) is used as the hydrolase.

5. The process as claimed in claim 1, wherein the reaction is carried out at 10° to 50° C.

6. The process as claimed in claim 1, wherein the reaction is carried out at a pH of 5 to 8.

* * * * *